US008021045B2

(12) United States Patent
Foos et al.

(10) Patent No.: US 8,021,045 B2
(45) Date of Patent: Sep. 20, 2011

(54) INTEGRATED PORTABLE DIGITAL X-RAY IMAGING SYSTEM

(75) Inventors: David H. Foos, Webster, NY (US); Xiaohui Wang, Pittsford, NY (US); Kevin J. Hobert, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 93 days.

(21) Appl. No.: 12/581,912

(22) Filed: Oct. 20, 2009

(65) Prior Publication Data
US 2010/0104066 A1 Apr. 29, 2010

Related U.S. Application Data

(60) Provisional application No. 61/108,630, filed on Oct. 27, 2008.

(51) Int. Cl.
*H05G 1/02* (2006.01)
*H05G 1/64* (2006.01)

(52) U.S. Cl. ............ 378/198; 378/62; 378/162; 378/165

(58) Field of Classification Search .................. 378/62, 378/91, 162, 165, 196, 197, 198
See application file for complete search history.

(56) References Cited

U.S. PATENT DOCUMENTS

| | | | |
|---|---|---|---|
| 6,475,146 B1 * | 11/2002 | Frelburger et al. | 600/437 |
| 7,006,600 B1 * | 2/2006 | Krema et al. | 378/98.7 |
| 7,016,467 B2 | 3/2006 | Brooks | |
| 7,038,588 B2 * | 5/2006 | Boone et al. | 340/573.1 |
| 7,309,159 B2 * | 12/2007 | Watanabe | 378/198 |
| 7,343,565 B2 * | 3/2008 | Ying et al. | 715/780 |
| 7,438,470 B2 | 10/2008 | Koren | |
| 7,502,445 B2 * | 3/2009 | Shi et al. | 378/115 |
| 7,549,961 B1 * | 6/2009 | Hwang | 600/440 |
| 7,573,034 B2 | 8/2009 | Heath et al. | |
| 2004/0086077 A1 * | 5/2004 | Moriyama | 378/29 |
| 2005/0265267 A1 * | 12/2005 | Hwang | 370/310 |
| 2007/0189462 A1 * | 8/2007 | Spahn | 378/193 |
| 2008/0103509 A1 | 5/2008 | Goldbach | |
| 2008/0144777 A1 | 6/2008 | Wilson | |
| 2009/0041325 A1 | 2/2009 | Luo | |
| 2009/0214099 A1 | 8/2009 | Merlet | |
| 2009/0274272 A1 | 11/2009 | Martin et al. | |

* cited by examiner

*Primary Examiner* — Allen C. Ho

(57) ABSTRACT

A mobile digital radiography system of a type including a mobile x-ray source; a mobile computer, the computer having a display for radiographic images and related information; a digital radiography detector, the detector and x-ray source in communication with and under control of the computer, means operatively associated with the computer for sending and receiving data concerning a patient, such data including diagnostic results, diagnostic images and requests for additional services, to and from separate image archiving and information systems; means operatively associated with the computer for comparing data from separate hospital image archiving and radiology information systems from a prior examination of a patient with data from a current examination of a patient using the mobile digital radiography system; and means operatively associated with the computer for aiding bedside interpretation of a patient's condition in view of the comparing of data from prior and current examinations.

24 Claims, 15 Drawing Sheets

INTEGRATED PORTABLE DIGITAL X-RAY IMAGING SYSTEM

CROSS REFERENCE TO RELATED APPLICATIONS

Priority is claimed from U.S. Ser. No. 61/108,630, provisionally filed on Oct. 27, 2008, entitled "INTEGRATED PORTABLE DIGITAL X-RAY IMAGING SYSTEM", in the name of David H. Foos et al., commonly assigned and incorporated herein by reference.

FIELD OF THE INVENTION

The invention relates generally to diagnostic imaging and in particular to portable X-ray imaging systems. More specifically, the invention relates to a digital X-ray imaging system that integrates imaging, quality control, and data access functions for improved delivery of diagnostic imaging services.

BACKGROUND OF THE INVENTION

Portable chest radiography is a widely performed radiographic exam in the intensive care unit (ICU). Radiographs of patients in the ICU are captured for a number of reasons, including verification of the placement of life support tubing, line, wires, sensors, and related devices and as part of routine monitoring of a patient's condition.

Flat panel digital radiography (DR) systems are rapidly being introduced into the portable x-ray imaging environment. Advantageously, DR receivers directly convert radiation energy received into digital data, without the need for separate scanning or processing equipment. Because these devices generate image data directly, they are able to provide both a high-resolution image for diagnostic purposes and a lower-resolution preview image that can be used in the clinical environment and for quality control (QC) purposes, facilitating workflow for radiographic technologists in the ICU. Lower resolution images, for example, can be used to quickly provide sufficient information about the positioning of tubing and other life support devices needed in intensive care situations.

Currently, portable DR systems include a portable x-ray machine that generates x-ray radiation, a flat panel DR receiver or detector that is tethered by cable to the portable x-ray machine, a host computer for processing the captured image, and a monitor for assisting image QC. In general, however, existing portable x-ray systems are self contained, tending to be somewhat bulky and inflexible.

In a typical workflow for portable radiography, a technologist is provided with a hard-copy worklist that indicates imaging requirements for various patients in the ICU. The technologist captures the images of all patients on the worklist, then at some convenient opportunity (usually after completing the rounds), downloads the captured images to a PACS (Picture Archive Communications System) for subsequent clinical and diagnostic interpretation. Unfortunately, this conventional workflow pattern can sometimes be poorly suited to the requirements of patient care. The need to upload image data to the PACS or other archive system means that interpretation of the obtained images cannot be performed on-site, but need coordination with off-site diagnosticians. Urgent care situations require personal intervention and are handled as exceptions rather than accommodated in the workflow. It can be difficult for the clinical staff to determine the status of a worklist request until some time after the image is obtained. There can be an undesirable delay in obtaining response information for problems of tube and line placement. Significant information that can help to guide the imaging process is not made available to the technologist unless it is provided in the worklist data. In addition, quality control (QC) suffers, since the technologist waits for off-site processing and response in order to determine whether or not an obtained image is usable for diagnostic purposes.

There have been a number of attempts to improve the delivery of portable radiography services in the ICU environment and to provide bedside support for interpreting imaging results and improving patient care. For example, commonly assigned U.S. Pat. No. 7,573,034 entitled "MOBILE RADIOGRAPHY IMAGE RECORDING SYSTEM" to Heath et al. describes a portable radiography system with a network connection for providing an electronic worklist request, for helping to control various imaging functions, for accessing patient records, and for collecting information related to image capture. U.S. Pat. No. 7,016,467 entitled "MOBILE DIGITAL RADIOGRAPHY X-RAY APPARATUS AND SYSTEM" to Brooks describes a portable digital radiography system with a computer for control of the image capture process and for uploading image data from a DR detector to a networked Picture Archiving and Communications System (PACS) or other archive system.

While solutions such as these can help improve the delivery and efficiency of mobile DR imaging for ICU and other environments, however, further improvements to workflow and more effective delivery of imaging services are still needed. With existing solutions, for example, the technologist does not have ready access to some types of information that can help to provide images that are more acceptable and useful to the diagnostician. This can include, for example, information on prior images obtained and on the imaging techniques used for earlier exams. Workflow remains cumbersome and assignment of technologist tasks still remains a largely manual process in many ICU environments. It can be difficult for the technologist to determine what is needed for each patient and to prioritize the sequence of images that are needed accordingly. There is still a tenuous link between useful information, such as technique settings used previously, and what is needed in order to obtain a new image for the same patient.

Overall, the need for improved support for bedside personnel has not been addressed by conventional solutions, so that back-and-forth communications with off-site staff may occur in order to detect problems, such as tube positioning problems. Systems that perform such complex image analysis functions often desire the full-resolution image and employ considerable computing power and are designed to show results on high-resolution displays that are used for diagnostic purposes rather than for quick clinical assessment. Conventional approaches have failed to take advantage of the full range of information about the patient and about patient images that can be made available to the imaging technologist and to the ICU staff.

Thus, even though some advances have been made, it can be seen that there is a need for a portable digital x-ray imaging system that more effectively supports the requirements of ICU imaging and the needs of bedside clinical personnel.

SUMMARY OF THE INVENTION

It is an object of the present invention to advance the art of diagnostic imaging and workflow using portable x-ray imaging systems. It is a further object of the present invention to provide clinical personnel with improved tools for bedside analysis of a patient's condition using information obtained from diagnostic images and other diagnostically relevant data. With these objects in mind, the present invention provides, in a mobile digital radiography system of a type including a mobile x-ray source; a mobile computer, the computer having a display for radiographic images and related information; a digital radiography detector responsive to x-rays emitted from the source that have passed through a portion of a patient's body, the detector and x-ray source being in communication with and under control of the computer, the improvement comprising: means operatively associated with the computer for sending and receiving data concerning a patient, such data including diagnostic results, diagnostic images and requests for additional services, to and from separate hospital image archiving and radiology information systems; means operatively associated with the computer for comparing data from separate hospital image archiving and radiology information systems from a prior examination of a patient with data from a current examination of a patient using the mobile digital radiography system; and means operatively associated with the computer for aiding bedside interpretation of a patient's condition in view of the comparing of data from prior and current examinations.

A feature of the present invention is the use of one or more detachable displays that provide the combined functions of image display surfaces, information displays, and data entry work-pads for providing instructions and for recording and displaying patient information.

It is an advantage of the present invention that it provides a portable integrated solution for diagnostic imaging in ICU and other urgent care clinical environments.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
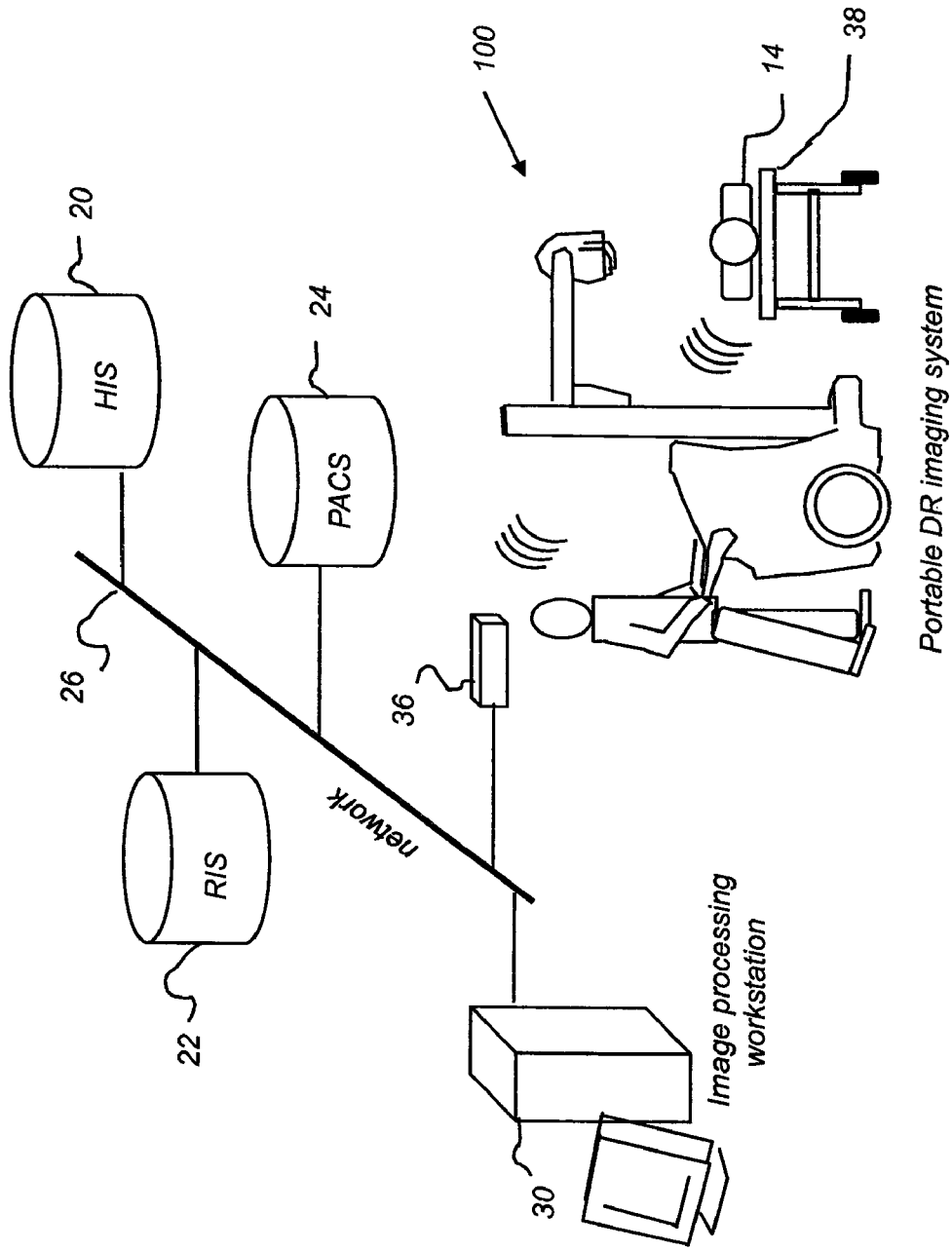
FIG. 1 shows a mobile digital radiography system according to an embodiment of the present invention.

The following is a detailed description of the preferred embodiments of the invention, reference being made to the drawings in which the same reference numerals identify the same elements of structure in each of the several figures.

The schematic block diagram of FIG. 1 shows a mobile digital radiography system 100 that obtains images of a patient 14 in an ICU or other facility and communicates with a separate/different/various medical archiving or radiology databases over a network 26. Among the medical databases that communicate over network 26 are a Hospital Information System (HIS) 20, a Radiology/Radiologist Information System (RIS) 22, and a PACS 24. (Such databases can also be referred to as image archiving and radiology information systems, or as archiving and information systems.) In addition, one or more optional image processing workstations 30 also receive images from mobile digital radiography system 100. Mobile digital radiography system 100 has a wireless interface 36 to network 26, typically connecting to a wireless hub or similar data communications interface device. The use of a wireless interface, while not essential to system operation, offers significant advantages for system usability, flexibility, and information access, as described subsequently.

Figure 2:
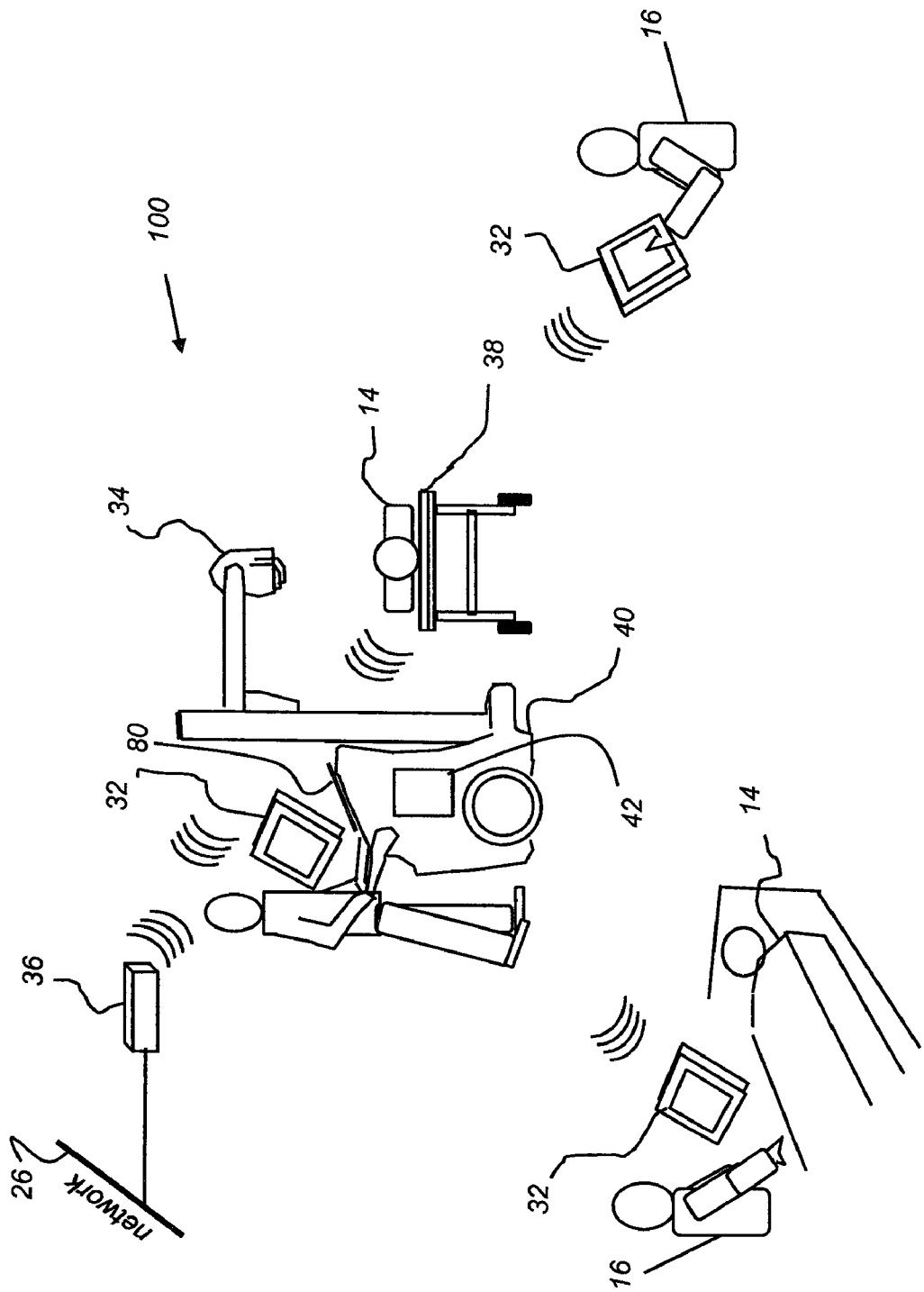
FIG. 2 shows distributed access to the mobile digital radiography system for interpreting or entering information.

FIG. 2 shows a schematic block diagram of mobile digital radiography system 100 in one embodiment. A cart 40 has an x-ray source 34 with the generator and related components for passing x-ray radiation through a portion of the patient's body and on to a DR detector 38. A computer 42, shown within cart 40 in this embodiment, provides the control logic for controlling a number of functions, including controlling the x-ray generation from x-ray source 34, obtaining the digital image data from DR detector 38, and controlling the transfer of data with network 26 and with one or more display interface units 32. An optional secondary display 80, such as a high-resolution display monitor, is also provided as part of cart 40.

As shown in FIG. 2, a number of detachable display interface units 32 can be used as part of mobile digital radiography system 100 for communication of patient images, patient data and history, instructions, and other data. Display interface unit 32 provides access to mobile digital radiography system 100 in a number of ways. The technologist uses display interface unit 32 for obtaining workflow sequence instructions, obtaining information relevant to obtaining a suitable image for each patient, for controlling the imaging apparatus itself, and for initial quality control (QC) checks of image quality. An attending physician 16 uses display interface 32 to enter instructions and work orders for the image or images needed for a particular patient. The ICU staff use display interface 32 to check the status of imaging requests and to obtain notification that requested images have been obtained. Display interface 32 also serves for interpretation of the patient condition for another physician 16 at the bedside, allowing a comparison with data from prior examinations and allowing interpretation of proper positioning of tubing or other lines, for example.

Figure 3:
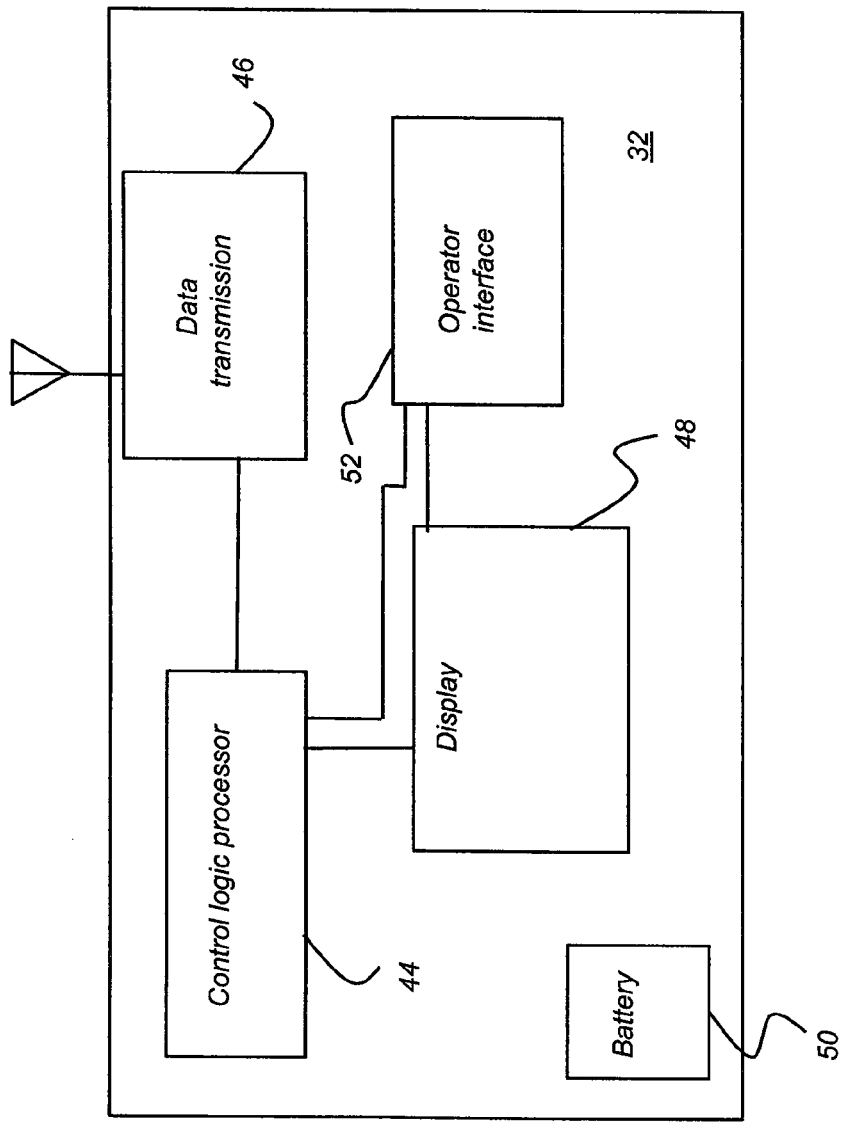
FIG. 3 is a schematic diagram of a display interface unit in one embodiment.

FIG. 3 is a schematic diagram showing components of display interface unit 32 in one embodiment. Display interface unit 32 provides a housing adapted to be held by an operator of the digital radiography system. Its housing encloses logic processing components, a display 48, means for receiving image and other patient data in either a wireless or a cabled mode, and means for comparing data in some way. Display interface unit 32 also provides a number of utilities for aiding bedside interpretation, as described in more detail subsequently. Display 48, such as a liquid-crystal or other compact display type, is provided. For command entry, a touchscreen or keypad (not shown) is used. A control logic processor 44 provides the needed control logic at least for basic display interface unit 32 functions, including control of display 48 and data transmission to and from a wireless interface 46. A battery 50 provides on-board power for display interface unit 32 operation. Preferably, battery 50 is a rechargeable battery, needed only when display interface unit 32 is detached from cart 40 (FIG. 2). Control logic processor 44 is a separate microprocessor or similar logic circuitry device in one embodiment, coordinating its control functions with computer 42 on cart 40. In another embodiment, control logic processor 44 provides all of the needed control logic for the complete mobile digital radiography system. Display interface unit 32 further includes operator interface 52.

Wireless connection is advantageous and practical for the bedside environment; however, optional data cable and power cable (not shown) are provided in one embodiment, enabling use of display interface unit 32 where battery power fails or where the wireless communication link is not operating properly, such as due to noise from external equipment, for example.

Figure 4:
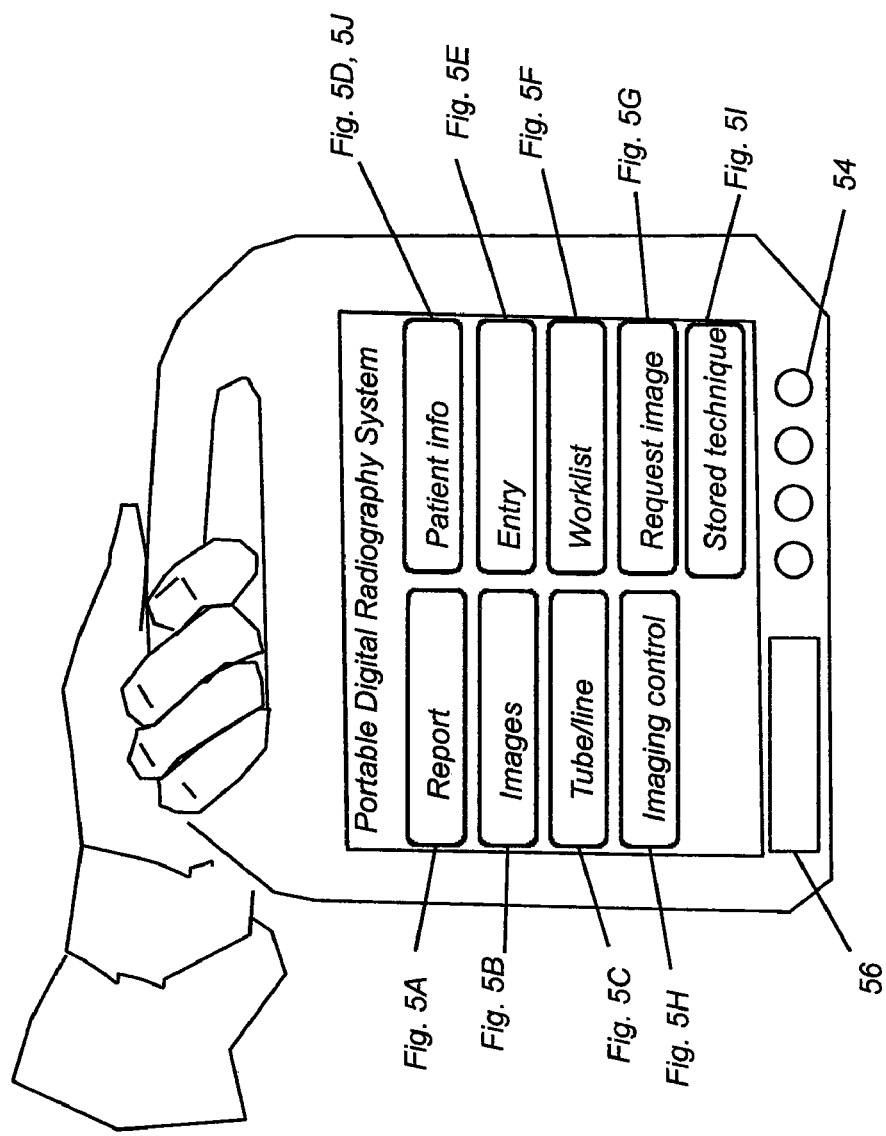
FIG. 4 is a plan view showing a hand-held display interface unit detachable from the mobile digital radiography system.

FIG. 4 shows a hand-held display interface unit 32 that is detached from mobile digital radiography system 100 and shows a displayed menu of exemplary control and reporting functions for this device. The user selects one of the available operating modes, such as by touchscreen entry or using one or more controls 54 or a keypad 56 that are mounted on or otherwise associated with display interface unit 32. In an alternate embodiment, audible instructions are used to select various display and control options. A mouse or other pointer could alternately be used to enter instructions and responses using display interface unit 32. Other known user interface utilities could be employed for manipulating objects on the screen, including cascaded displays or tabs and including slide-away images or displays that respond to operator touch for panning or changing position, for example.

The overall function of display interface unit 32 as a clinical tool includes aiding interpretation of a patient's condition. This can be distinguished from diagnosis, which can employ high-resolution displays and image processing of the complete set of image data and which is generally performed on high-end computer workstations. By comparison, clinical interpretation functions can be performed by viewing images that are presented at a relatively lower image resolution, but that have sufficient information to guide timely treatment and urgent care requirements, such as those typical to the ICU environment.

Figure 5A:
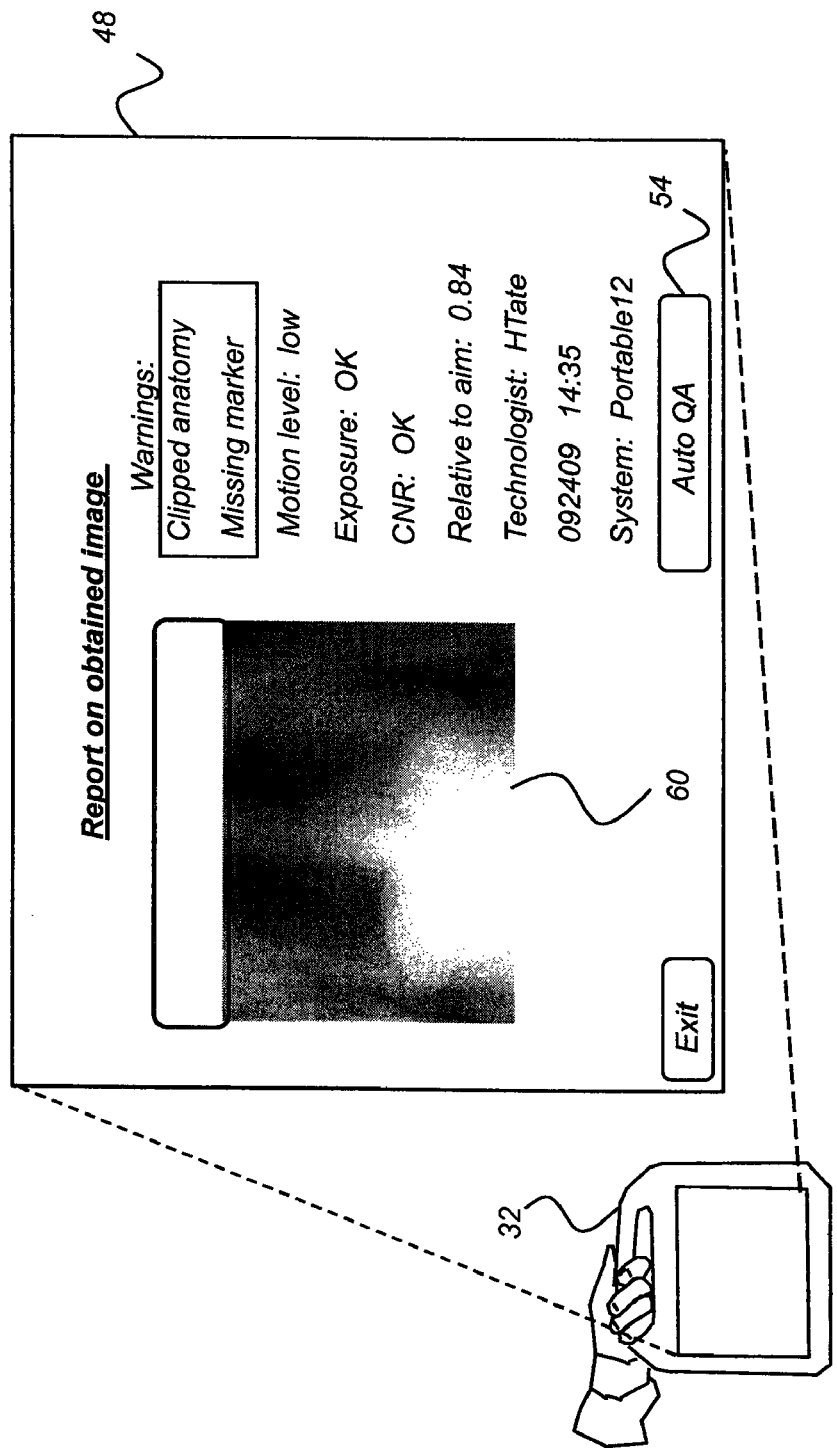
FIG. 5A is a plan view showing a mode of operation for imaging reporting.

By way of example and not of limitation, FIGS. 5A through 5J show various operational modes of display interface unit 32. In FIG. 5A, an image reporting mode is shown. This mode may display a reduced-resolution version of an obtained image 60 and alerts the operator to a detected error or problem that concerns an image previously taken. For example, problems such as clipped anatomy, missing markers, excessive exposure, excessive motion, image artifacts, or other imaging anomalies can be detected and shown, following automatic processing. These can be detected by image processing that is performed by control logic processor 44 (FIG. 3), or by computer 42 (FIG. 2), or by networked image processing workstation 30 (FIG. 1). Imaging characteristics such as Contrast to Noise Ratio (CNR) and exposure levels can also be analyzed and reported at any suitable processor in the image acquisition and processing chain. The image report can also display data such as image exposure relative to an aim exposure level. Information identifying the technologist and system can be useful for obtaining further data or clarification about the exam. An optional control 54 also enables automatic quality assurance routines to be executed on the obtained image data, with reports provided for display.

Figure 5B:
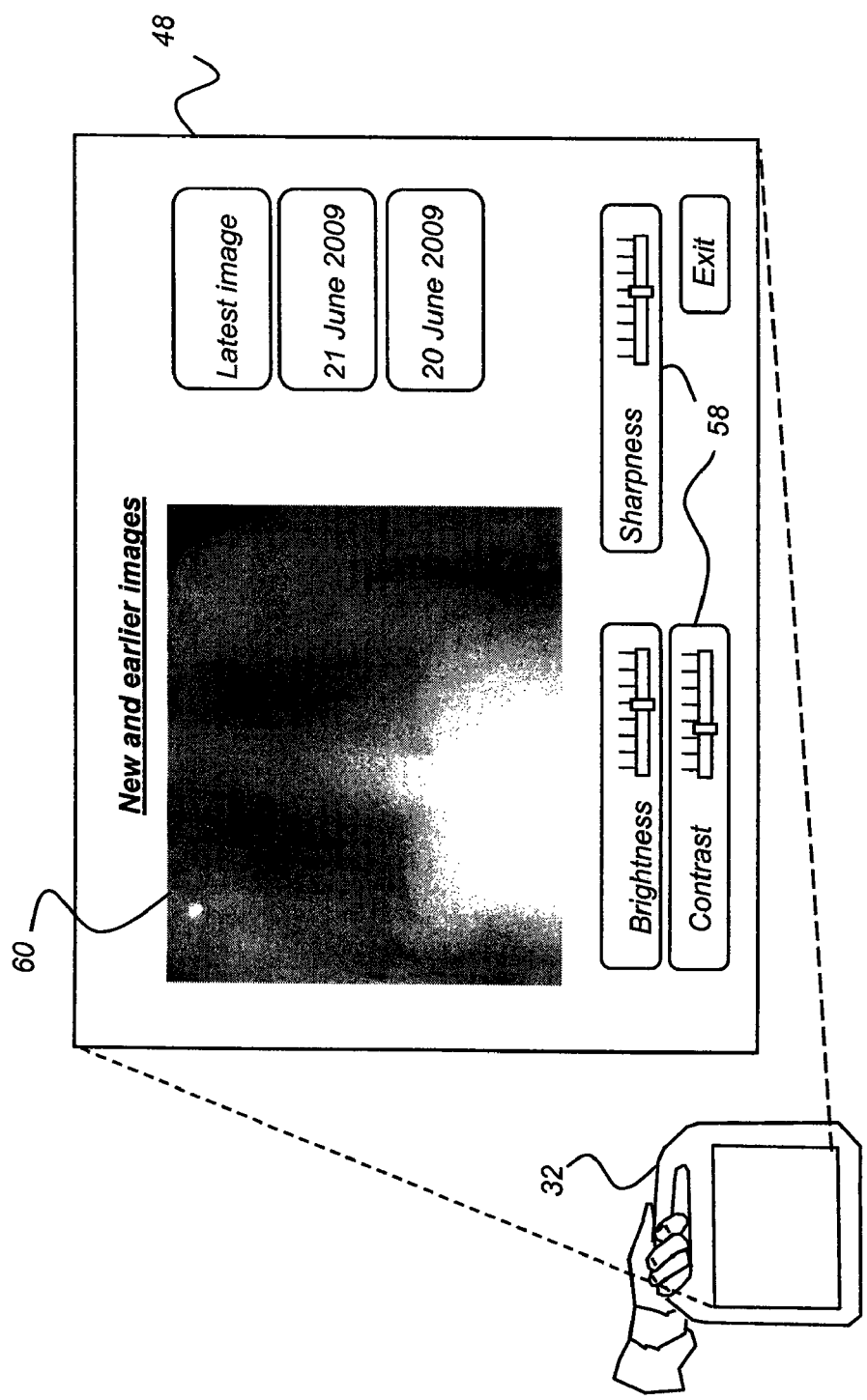
FIG. 5B is a plan view showing a mode of operation for displaying one or more images for the same patient.

The plan view of FIG. 5B shows a display mode for displaying one or more images 60 that have been obtained for the same patient, such as at separate/different times and locations. Using this tool with wireless access to image databases, patient images as well as patient history can be tracked and made available to the attending medical personnel at the patient bedside, without the need for separate requests of patient records. This helps to aid bedside interpretation of a patient's condition by allowing comparison of data from prior and current examinations, for example.

In addition to patient history, display mode also allows display of images with different image processing treatment. Even at the lower-resolution levels provided for such a hand-held device, some imaging characteristics such as overall contrast and image consistency can be visually evaluated. Controls 58 in FIG. 5B provide mechanisms for adjusting brightness, contrast, sharpness of images, and other image attributes that control display presentation. Automatic processing can alternately be used for any of these and other image attributes. Significant changes in patient condition can be detected by a processor at any point along network 26 (FIG. 1) for reporting to the attending physician in the ICU using this feature. Functions for automatic processing include various features for computer-aided diagnosis and for pneumothorax enhancement in one embodiment. Image comparison can be automatically performed and the results used to provide data as a basis for providing useful clinical information.

Figure 5C:
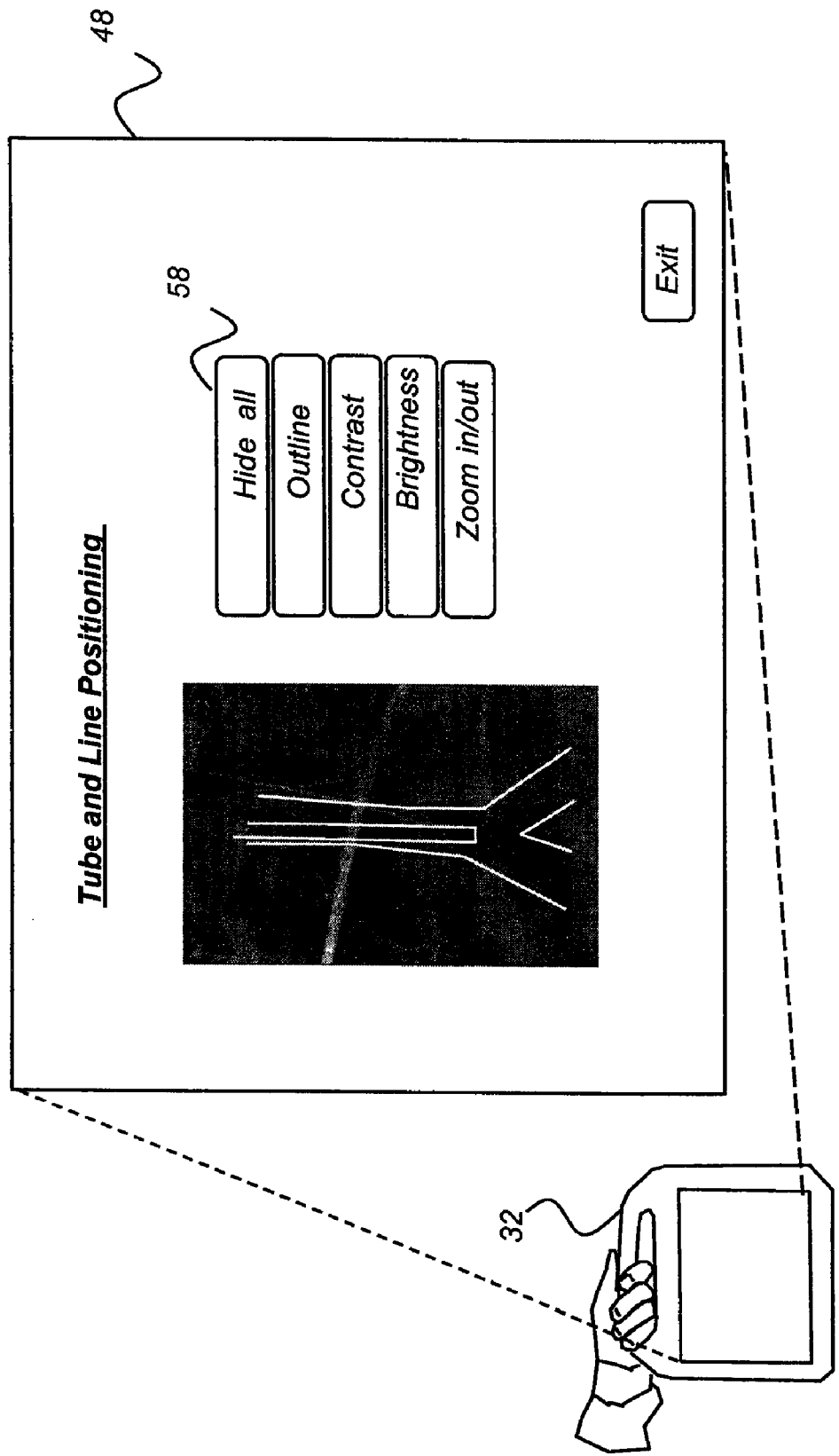
FIG. 5C is a plan view showing a mode of operation for displaying tubing and line position.

FIG. 5C shows the use of display interface unit 32 for displaying various life support line visualizations that have been automatically generated, such as tubing and line position and catheter placement. Image processing algorithms that support this function can be provided at any suitable processor in the network, including at control logic processor 44 within display interface unit 32. However, because this detection can be a complex computational task requiring substantial control logic and memory resources, it is more likely that tubing detection would be implemented at image processing workstation 30 (FIG. 1) and results formatted for low-resolution display and downloaded to display interface unit 32 when requested. A set of controls 58 are provided for manipulating the image display to help improve the visibility of lines and tubing in the radiographic image. In one embodiment, visualization settings for life support line presentations can be pre-set, so that settings and selections found most readily usable to the attending medical team can be employed, such as using them as default settings, for example.

Figure 5D:
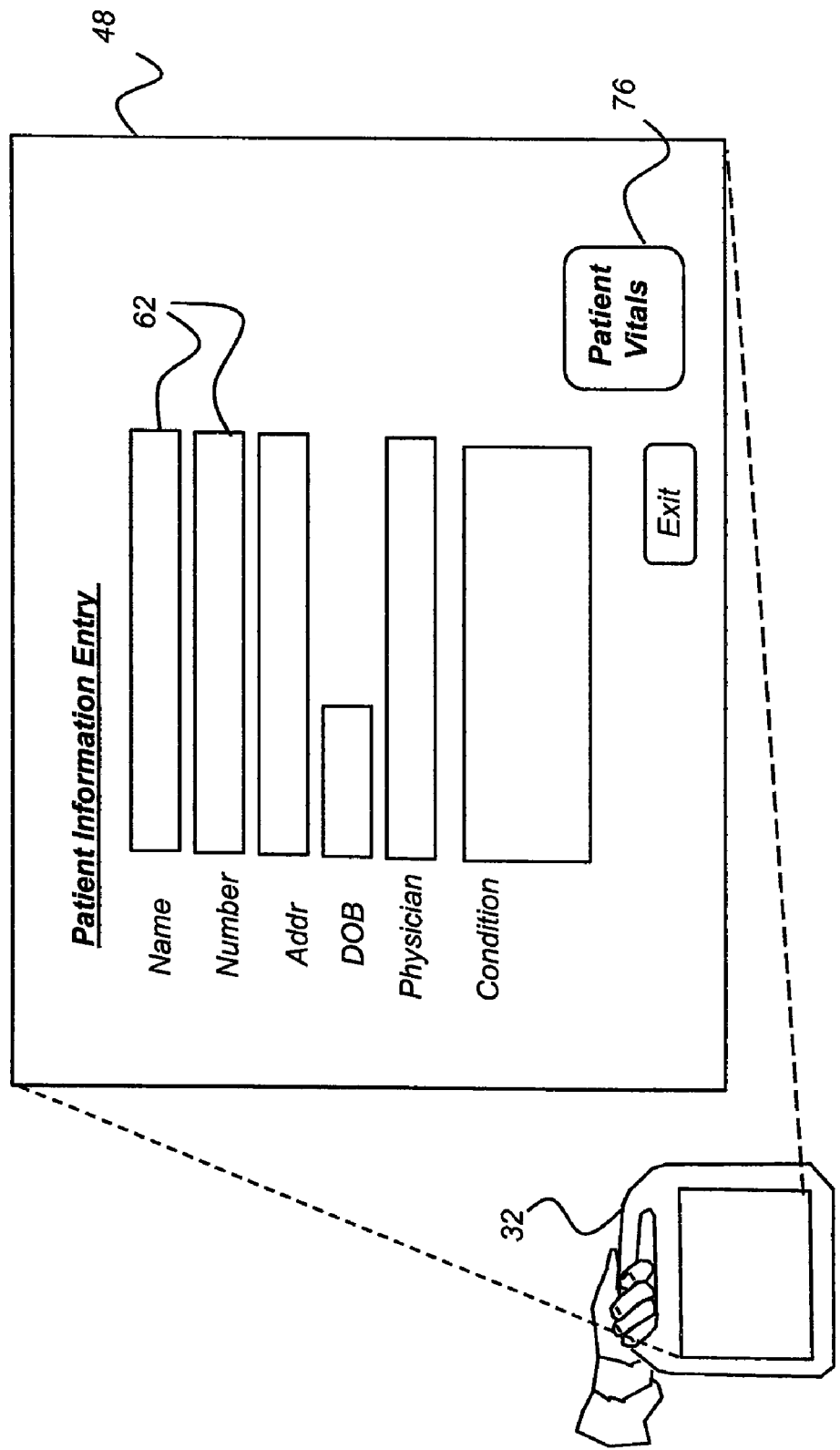
FIG. 5D is a plan view showing a mode of operation for entering patient information by the technologist or other personnel.

The plan view of FIG. 5D shows an exemplary entry screen for patient information and update, available on display interface unit 32. A keyboard, keypad, or other set of controls, as described previously, enable entry and update of patient information in one or more data fields 62. In one embodiment, audible entries are recorded for voice-actuated data entry and entered data are displayed in the indicated fields 62. The displayed information, downloaded from the hospital information system, HIS 20 in FIG. 1, can then be uploaded following editing, to keep the patient database current. Data entered can include various inputs to a structured report, for example. Patient vital information can be accessed at a control 76, such as by being downloaded from a networked HIS database, for example. In one embodiment, entry of the patient Name or Number fields automatically populates other information fields for verification by the entering user. This occurs, for example, once the patient records can be uniquely identified from the user's data entry. For example, the entry of a unique Social Security number is sufficient for prompting a search of medical data and image databases in order to obtain information about the patient and, optionally, to ascertain whether or not other relevant diagnostic images are stored for that patient.

Figure 5E:
FIG. 5E is a plan view showing a mode of operation for entering medical information for a patient using the display interface unit.

FIG. 5E shows a checklist 64 that can be used by an attending nurse or physician to provide useful clinical information relative to the condition of the patient, including pathology and treatment data. Information in this format is particularly well-suited for touchscreen entry.

Figure 5F:
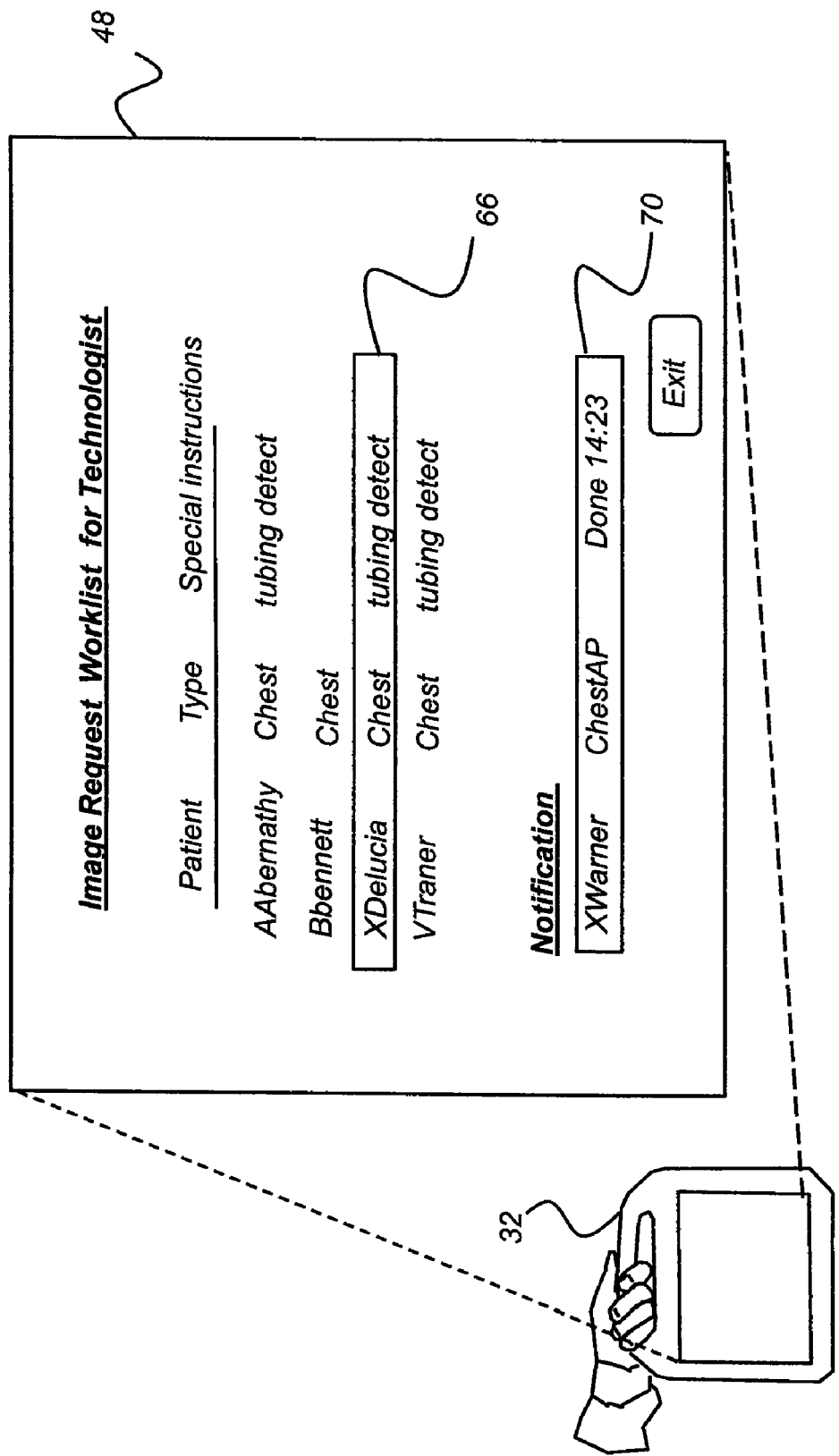
FIG. 5F is a plan view showing a mode of operation for displaying a technologist worklist for obtaining images.

FIG. 5F shows a mode of operation for displaying a technologist worklist for obtaining images. The worklist can include a priority indicator 66, such as a highlighting using color or text on a reversed background or using a blinking entry, for example. Optional priority indicator 66 can be used to direct the attention of the technologist to critical images that have priority over others. A notification 70 can also be provided as part of the worklist, or as a separate signal or message appearing on any of the display screens, indicating when image data has been obtained and the image is available for viewing. In one embodiment, a notification signal is provided for each image obtained. In an alternate embodiment, priority settings assigned to the image determine how notification is provided. Notification 70 may also indicate a potential problem detected by an automated diagnostic process that operates on the obtained image data and may indicate the need for radiologist review, for example. A beeping or other audible prompt may also be provided to indicate that a requested image has been obtained and is ready for viewing.

Figure 5G:
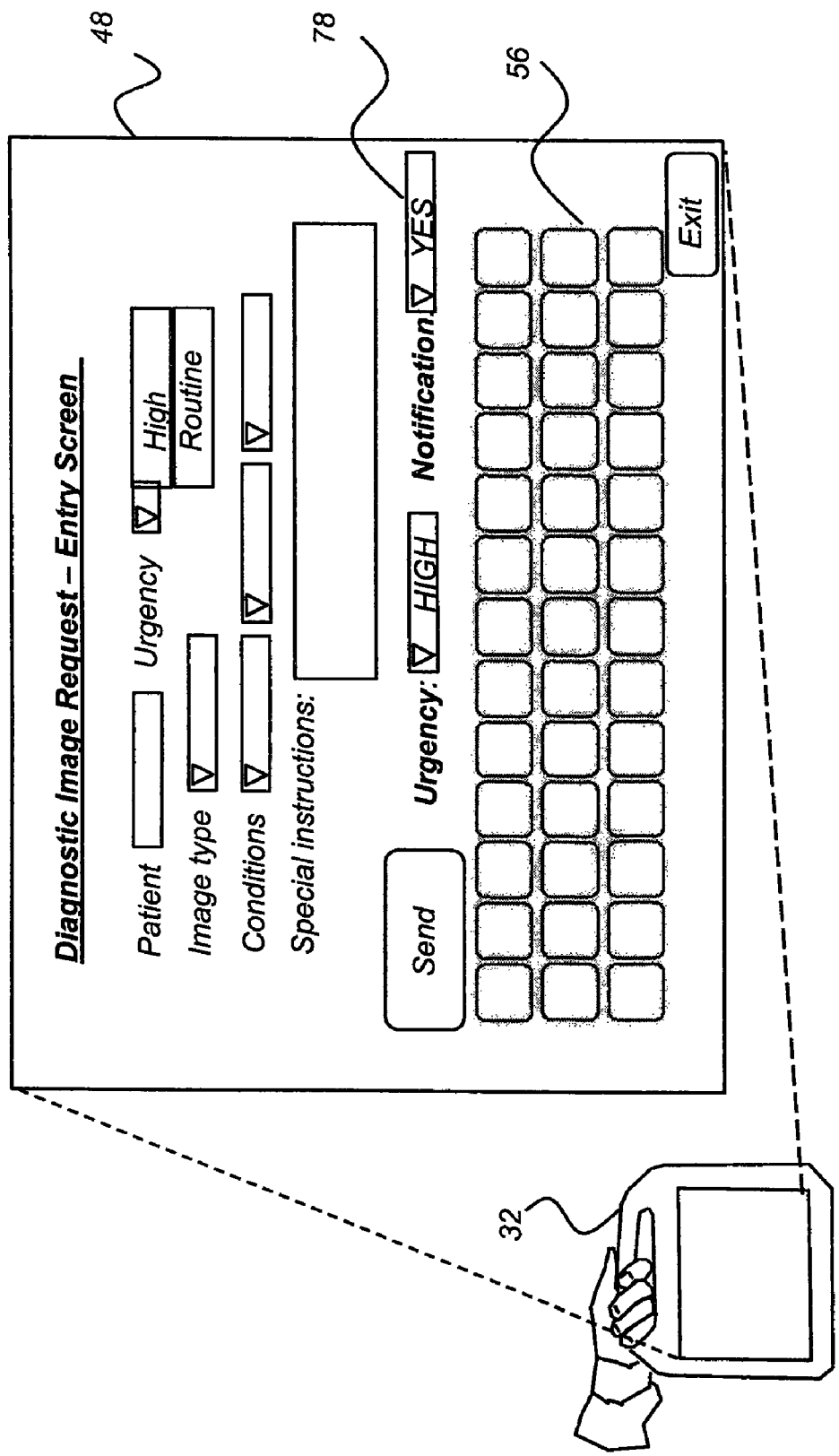
FIG. 5G is a plan view showing a mode of operation for entering a request for imaging from the mobile DR system.

FIG. 5G shows an operating mode in which display interface unit 32 obtains and processes a request for one or more diagnostic images or for additional services, such as laboratory tests or procedures, for example. The attending physician can use this as a convenient means for entering worklist items, for example, or for indicating the priority of pending imaging tasks. In the embodiment of FIG. 5G, on-board keypad 56 is provided for obtaining authorized entries. Optional controls 78 are provided to indicate a selected urgency level and to indicate what type of notification might be needed.

Figure 5H:
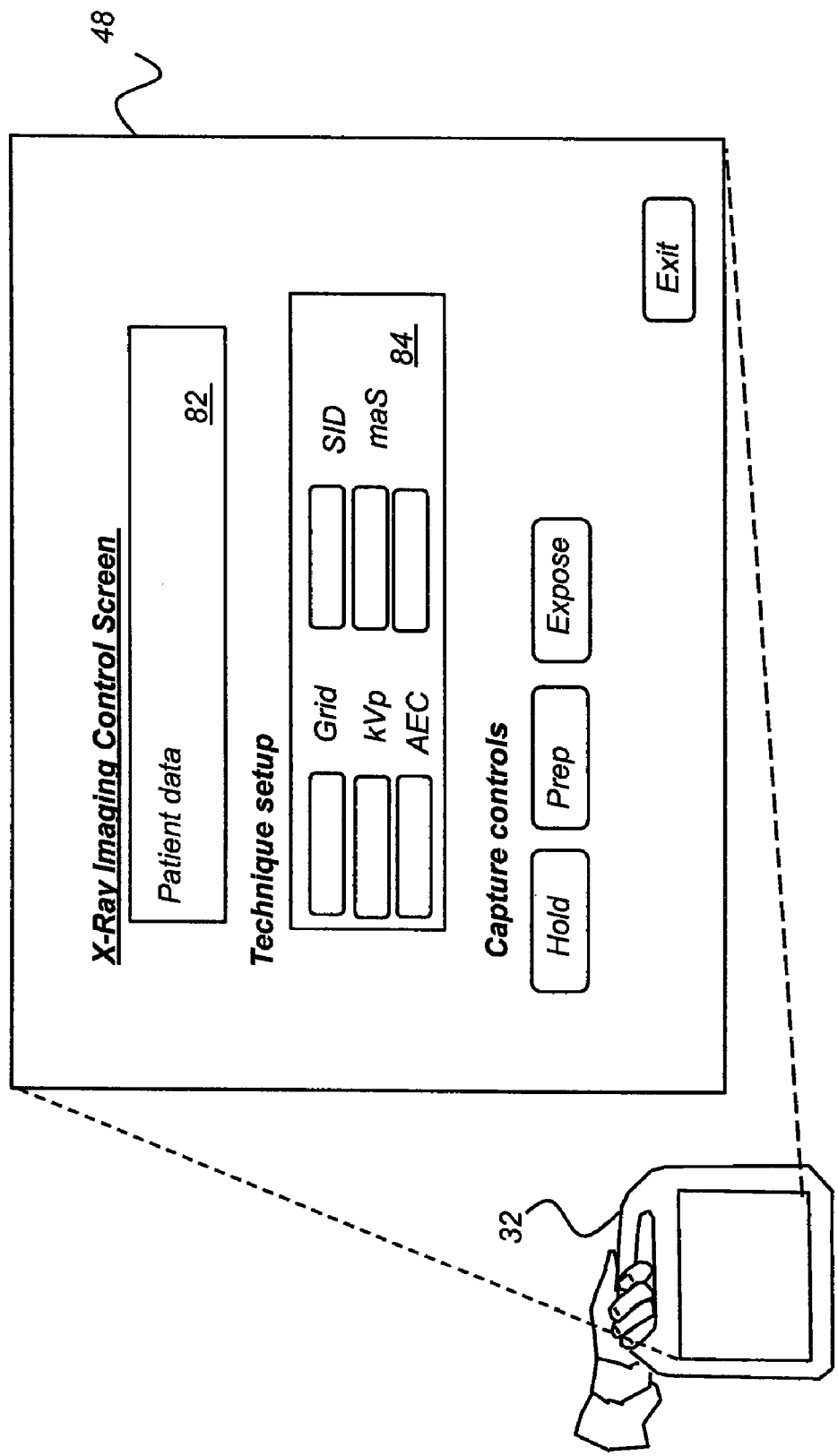
FIG. 5H is a plan view showing a mode of operation for displaying controls and parameter entry for the imaging process.

FIG. 5H shows a mode of operation in which controls for the image capture process itself are displayed. In this mode, the technologist uses display interface unit 32 as a control panel for imaging functions, with various controls that set up exposure variables (technique setup) in a technique setup entry area 84. A patient data display area 82 displays information for the identified patient for whom the image is to be obtained. Image capture controls for receiver preparation and exposure are also provided on this display screen in one embodiment.

Figure 5I:
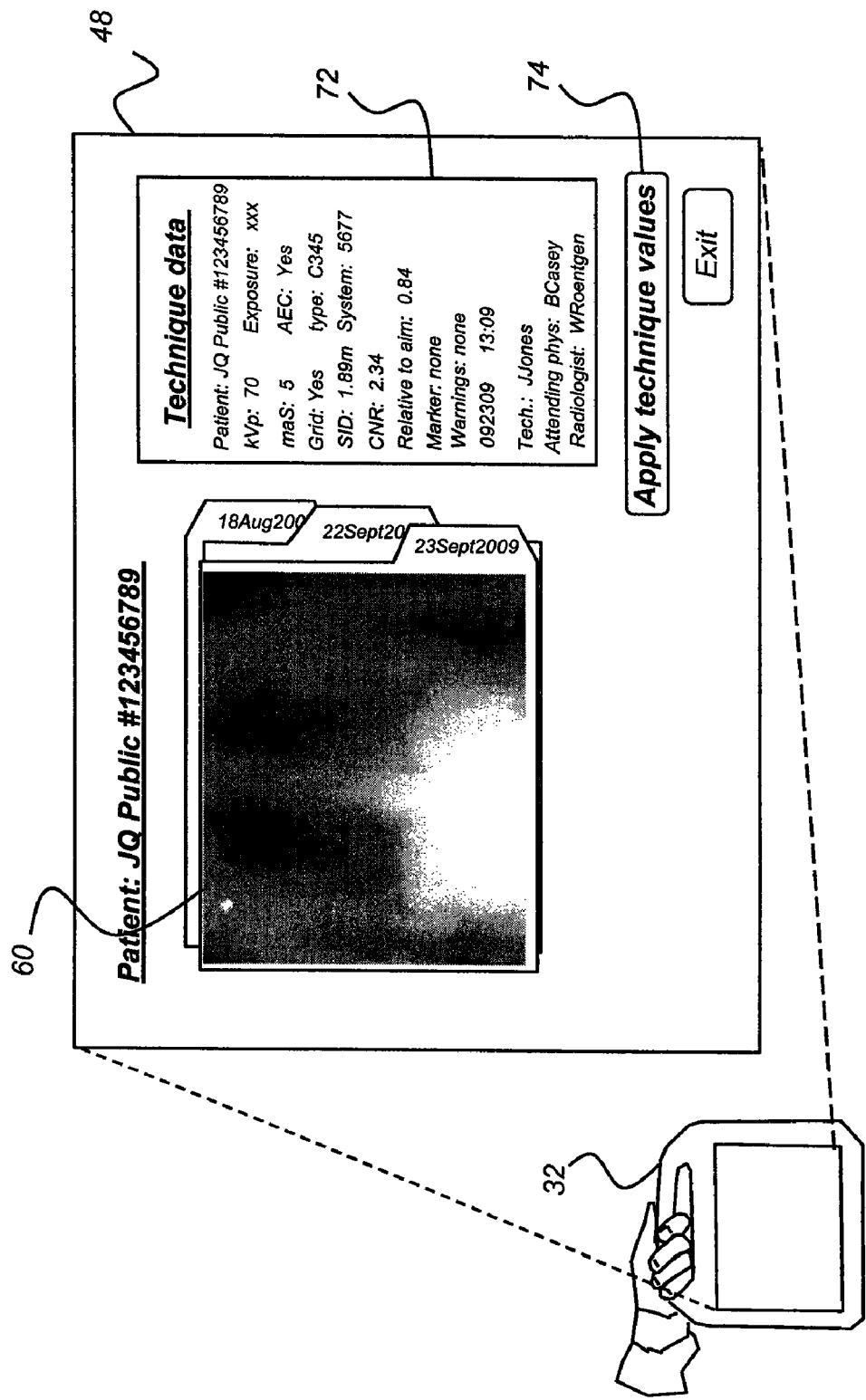
FIG. 5I is a plan view showing a mode of operation for displaying technique data used for earlier images of the patient.

FIG. 5I shows a display of currently stored images and corresponding technique data for an identified patient. This display facilitates comparison of images and data from separate/different systems. On this type of display screen, a smaller-scale image 60 displays, with corresponding technique data 72 also shown. The technique data is obtained from a medical database that links to images stored in the PACS archive in one embodiment. The viewer can use tabs or touch-based panning and dragging to select and position each of the stored images and view its technique data 72. A control 74 is provided that allows application of the active or displayed technique values for an upcoming image.

This selection populates the screen of FIG. 5H, for example, providing the stored values as defaults or as starting-points for technique value entry.

Figure 5J:
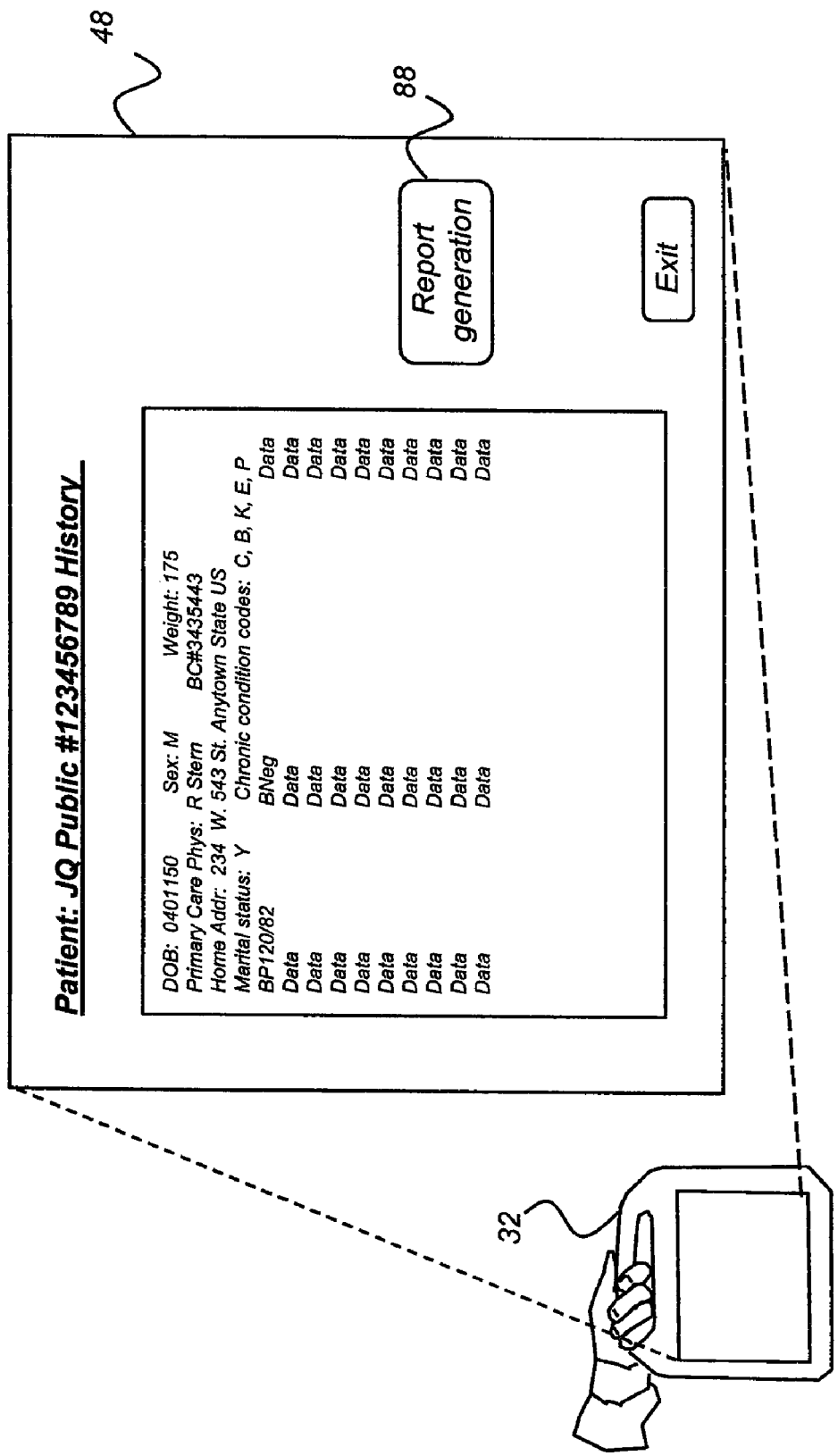
FIG. 5J is a plan view showing a mode of operation for displaying patient history.

FIG. 5J shows patient data obtained from a medical database and available for access by the attending physician or other authorized ICU personnel. Various data from the patient history can be displayed. A report generation button 88 enables the user to generate a structured report for current or historical patient images and related data, including use of data entered on any of the interface screens of FIGS. 5A-5J, for example. Voice actuation can also be used to provide input information for a structured report.

As can be seen from the example functions described with reference to FIGS. 5A through 5J, there can be a considerable body of image processing software and patient image data that are available at various networked processors. The apparatus and methods of the present invention make this information and capability more readily available and useful for meeting the needs of attending staff in ICU and related environments, where lower-resolution display may be sufficient for clinical assessment and urgent-care treatment. The apparatus and methods of the present invention work with patient image data that may also be examined by a radiologist at a later time, but provides this image data in a format that is more readily usable to ICU treatment staff.

Figure 6:
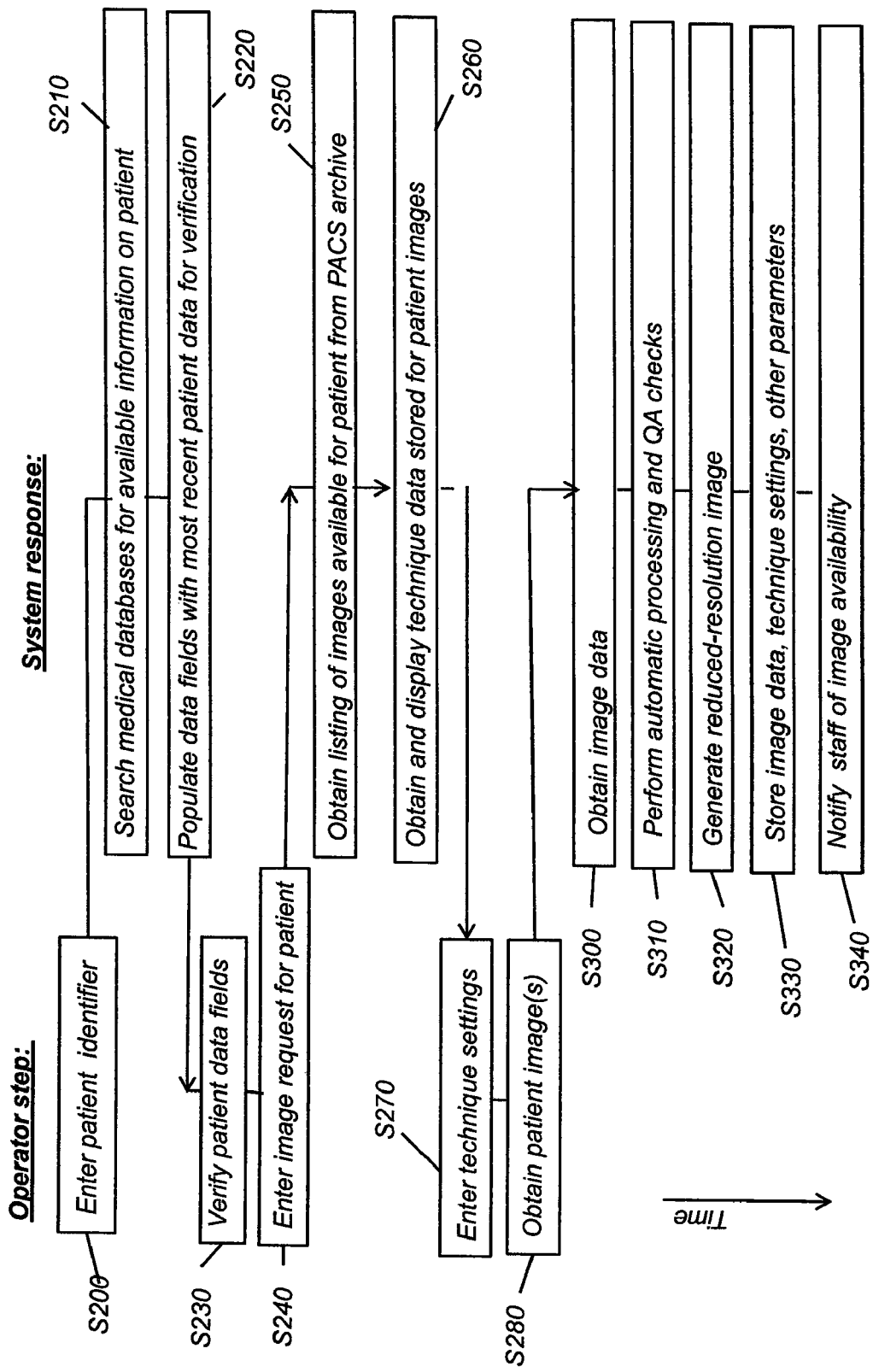
FIG. 6 is a logic flow diagram showing the sequence of operator steps and system responses for obtaining patient images according to one embodiment.

The logic flow diagram of FIG. 6 shows how image processing workstation 30 interacts with the technologist or other user and obtains information to support more efficient workflow and more effective treatment for ICU patients. Operator steps are in the column at the left; system responses are shown to the right. In a patient identifier entry step S200, the operator or technologist enters identifying patient information, such as on the interface screen shown in FIG. 5D. In response to step S200, a database search step S210 is executed, in which separate/various HIS and other medical databases are accessed and searched for obtaining any useful information about the patient. A data field population step S220 then populates data fields in the interface screen of FIG. 5D and elsewhere, such as in FIG. 5E for example, with historical or default patient data. Included in step S220 is information related to techniques used for obtaining other diagnostic images for the patient.

A verification step S230 accepts operator verification of patient identification information, allowing the operator or technologist to edit or re-enter any applicable information fields with suitable data for the patient. In an image request entry step S240, the clinical staff requests an image for the patient or requests additional services for the patient, such as using the interface screen of FIG. 5G. An image listing step S250 then obtains a listing of patient images that are available from PACS and other diagnostic image archival systems. These images can then be optionally downloaded for comparison against current images, as described previously with respect to FIGS. 5B and 5I. A technique data display step S260 obtains and displays technique data stored with the archived images, optionally populating data fields in technique setup, such as that shown in FIG. 5H. In a technique settings entry step S270, the technologist enters and edits the pre-populated data fields prior to image capture.

An obtain images step S280 is executed, in which the x-ray image is obtained, such as by technologist entry of commands from the screen of FIG. 5H. An obtain image data step S300 follows, during which the exposure occurs and diagnostic image data is formed and downloaded from the DR detector, as described earlier with reference to FIGS. 1 and 2.

Once the digital radiography image is obtained, a perform automatic processing step S310 is executed on the data, with presentation of processing results on the display. Automatic processing can include, for example, presetting visualization settings for life support line visualizations, as described earlier with reference to the interface screen of FIG. 5C. Automatic processing can also include adjusting variables for brightness, contrast, and sharpness of images or variables for enhancing the patient's pneumothorax, for example. Automatic processing can include features for computer assisted diagnosis, such as catheter placements. In addition, results of automatic quality assurance can be displayed on the interface screen of FIG. 5A, for example, and can include data from algorithms that check patient positioning, motion, exposure relative to an aim, clipped anatomy, contrast, and other variables and attributes of interest.

A generate reduced-resolution image step S320 then performs the resolution scaling of the image data in order to display the image on the lower-resolution screen of display interface unit 32, such as shown in screens of FIGS. 5A, 5B, 5C, and 5I, for example. A storage step S330 follows, in which image data, technique settings, and other data about the patient and related imaging parameters are stored for later access. An optional notification step S340 then informs members of the patient care staff that the needed image has been obtained and is available for clinical as well as diagnostic purposes.

In its various aspects, the method of the present invention executes on a computer workstation, host processor, microprocessor, or other type of computer system. Embodiments of the present invention may have the form of computer-implemented processes and apparatus for practicing those processes. Embodiments of the invention may also be embodied in the form of computer program code containing instructions embodied in tangible media, such as magnetic storage media such as a hard drive or removable magnetic media, optical storage media such as CD-ROMs, or any other computer-readable storage medium, wherein, when the computer program code for the embodiment is loaded into and executed by a computer or other host processor, the computer or processor becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a suitable logic processor or computer, the computer becomes an apparatus for practicing the invention. When implemented on a dedicated microprocessor, the computer program code segments configure the microprocessor to create specific logic circuits for program logic execution. One or more encoded signals that are provided as output can be used to display an image or data, store data or operator instructions, or upload or download images and data from networked computer systems, for example.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

14. Patient
16. Physician
20. Hospital Information System
22. Radiologist Information System
24. PACS
26. Network
30. Image processing workstation
32. Display interface unit
34. X-ray source
36. Wireless interface
38. DR detector
40. Cart
42. Computer
44. Control logic processor
46. Wireless interface
48. Display
50. Battery
52. Operator interface
54. Control
56. Keypad
58. Control
60. Image
62. Field
64. Checklist
66. Priority indicator
70. Notification
72. Technique data
74, 76, 78. Control
80. Display
82. Patient data display area
84. Technique setup entry area
88. Report generation button
100. Mobile digital radiography system
S200. Patient identifier entry step
S210. Database search step
S220. Data field population step
S230. Verification step
S240. Image request entry step
S250. Image listing step
S260. Technique data display step
S270. Technique settings entry step
S280. Obtain images step
S300. Obtain image data step
S310. Perform automatic processing step
S320. Generate reduced-resolution image step
S330. Storage step
S340. Notification step

What is claimed is:

1. A mobile digital radiography system comprising:
a mobile x-ray source for emitting x-rays through a portion of a patient's body;
a mobile computer having a display to display radiographic images and related information;
a digital radiography detector responsive to the emitted x-rays, the detector and x-ray source in communication with and under control of the computer;
means operatively associated with the computer for sending and receiving medical data concerning a patient;

means operatively associated with the computer for comparing medical data from two or more archiving and information systems of a prior examination of the patient with medical data from a current examination of the patient using the mobile digital radiography system; and means operatively associated with the computer for aiding bedside interpretation of a patient's condition in view of the comparing of the medical data from the prior and current examinations.

2. The mobile digital radiography system of claim 1, further comprising a housing adapted to be held in a hand of an operator of the digital radiography system, the housing enclosing the computer, the display, the means for receiving data, the means for comparing data and the means for aiding bedside interpretation.

3. The mobile digital radiography system of claim 1, wherein the means for aiding bedside interpretation includes functionality for automatic processing of diagnostic images and presentation of results of the processing on the display.

4. The mobile digital radiography system of claim 3, wherein the functionality for automatic processing includes features for adjusting brightness, contrast and sharpness of images presented on the display.

5. The mobile digital radiography system of claim 3, wherein the functionality for automatic processing includes preset visualization settings for life support line visualizations.

6. The mobile digital radiography system of claim 3, wherein the functionality for automatic processing includes features for pneumothorax enhancement.

7. The mobile digital radiography system of claim 3, wherein the functionality for automatic processing includes features for computer assisted diagnosis, such as catheter placements.

8. The mobile digital radiography system of claim 1, wherein the means for aiding bedside interpretation includes interactive functionality to facilitate report generation.

9. The mobile digital radiography system of claim 8, wherein the interactive functionality includes feature for inputs to a structured report.

10. The mobile digital radiography system of claim 9, wherein the inputs are actuated by voice.

11. The mobile digital radiography system of claim 9, wherein the inputs are actuated by touch-screen features on the display.

12. A method for operating a mobile digital radiography system of a type including a mobile x-ray source for emitting x-rays through a portion of a patient's body, a mobile computer having a display to display radiographic images and related information, and a digital radiography detector responsive to the emitted x-rays, the detector and x-ray source being in communication with and under control of the mobile computer, comprising:

receiving and sending medical data associated with the patient, such data including diagnostic results, diagnostic images and requests for additional services, from and to separate image archiving and radiology information systems;

comparing data from separate image archiving and information systems from a prior examination of a patient with data from a current examination of the patient using the mobile digital radiography system; and aiding bedside interpretation of a patient's condition in view of the comparing of data from prior and current examinations.

13. The method according to claim 12, wherein the step of aiding bedside interpretation includes automatic processing of diagnostic images and presenting of results of the processing on the display.

14. The method of claim 13, wherein the automatic processing includes adjusting brightness, contrast and sharpness of images presented on the display.

15. The method of claim 13, wherein the automatic processing includes presetting visualization settings for life support line visualizations.

16. The method of claim 13, wherein the automatic processing includes enhancing the patient's pneumothorax.

17. The method of claim 13, wherein the automatic processing includes features for computer assisted diagnosis, such as catheter placements.

18. The method of claim 12, wherein the step of aiding bedside interpretation includes interactive functionality to facilitate report generation.

19. The method of claim 18, wherein the interactive functionality includes features for inputs to a structured report.

20. The method of claim 19, wherein the inputs are actuated by voice.

21. The method of claim 19, wherein the inputs are actuated by touch-screen features on the display.

22. The method of claim 12 wherein receiving and sending data concerning a patient comprises transmitting data over a wireless interface.

23. The method of claim 12 wherein the digital radiography detector comprises a wireless communication interface.

24. A mobile digital radiography system comprising:
a mobile x-ray source for emitting x-rays through a portion of a patient's body;
a mobile computer having a display to display radiographic images and related medical information;
a digital radiography detector responsive to the emitted x-rays, the detector and x-ray source in communication with and under control of the mobile computer;
a communication link operatively associated with the mobile computer for accessing medical data from a current examination of the patient;
a communication link operatively associated with the mobile computer for accessing medical data from at least one prior examination of the patient from two or more medical databases;
wherein the mobile computer comprises a processor for comparing the medical data from the at least one prior examination with the medical data from the current examination; and
wherein the mobile computer comprises functions for providing bedside interpretation of a patient's condition based on the comparing of the medical data.

* * * * *